(12) United States Patent
Stenlund et al.

(10) Patent No.: US 7,610,158 B2
(45) Date of Patent: Oct. 27, 2009

(54) MEASURING DEVICE AND METHOD FOR MEASURING THE ARCHING OF AN ELONGATE BODY

(75) Inventors: Peter Stenlund, Stockholm (SE); Lars Wiklund, Sundsvall (SE)

(73) Assignee: Vendolocus AB, Stockholm (SE)

( * ) Notice: Subject to any disclaimer, the term of this patent is extended or adjusted under 35 U.S.C. 154(b) by 26 days.

(21) Appl. No.: 11/921,896

(22) PCT Filed: Jun. 1, 2006

(86) PCT No.: PCT/SE2006/050179

§ 371 (c)(1),
(2), (4) Date: Apr. 4, 2008

(87) PCT Pub. No.: WO2006/132591

PCT Pub. Date: Dec. 14, 2006

(65) Prior Publication Data

US 2008/0249719 A1 Oct. 9, 2008

(51) Int. Cl.
*G01B 3/00* (2006.01)
(52) U.S. Cl. ........................................ 702/33
(58) Field of Classification Search ........... 702/33, 702/41–43, 104, 158
See application file for complete search history.

(56) References Cited

U.S. PATENT DOCUMENTS

| | | |
|---|---|---|
| 3,760,636 A | 9/1973 | Serry |
| 3,922,908 A | 12/1975 | Stemsrud et al. |
| 4,055,061 A * | 10/1977 | Bayorgeon et al. ......... 72/31.02 |
| 4,164,875 A * | 8/1979 | Kantar et al. ................. 73/812 |

FOREIGN PATENT DOCUMENTS

WO WO7900207 A1 * 4/1979

* cited by examiner

*Primary Examiner*—Drew A Dunn
*Assistant Examiner*—Stephen J Cherry
(74) *Attorney, Agent, or Firm*—Buchanan Ingersoll & Rooney PC

(57) ABSTRACT

The present invention relates to a measuring device for measuring the arching of an elongate body. The measuring device includes an anvil member against which the elongate body is intended to be placed, a measure-collection member movable along the line of the longitudinal axis of the elongate body via a driving unit included in the measuring device, which measure-collection member is connected to a processor unit for the processing of measured values. Furthermore, the measuring device includes a force-transmission member for applying a predetermined force (F), where F>0 N, to the elongate body. The measure-collection member measures continuously, in abutment against and movement along the line of the longitudinal axis of the elongate body, a length (y) and a height (x) between the elongate body and the measuring device, and delivers a digital signal to the processor unit, which calculates the arching (A).

15 Claims, 7 Drawing Sheets

MEASURING DEVICE AND METHOD FOR MEASURING THE ARCHING OF AN ELONGATE BODY

FIELD OF THE INVENTION

The present invention relates, according to a first aspect, to a measuring device for measuring the arching of an elongate body.

According to a second aspect, the present invention relates to a method for measuring the arching of an elongate body.

BACKGROUND OF THE INVENTION

It is a problem that there is no reliable way of measuring the arching in general of an elongate body and in particular of a ski. In this context, an elongate body may, for instance, be different types of boards, beams, leaf springs, masts, pillars, posts, shafts, etc. Below, the description is focused on skis.

Nowhere there is two exactly similar skis, they are all individuals, since they are constructed as laminates consisting of composite and core material. Variables determining the properties of a ski based on substantially a composite material, as, e.g., arching curve, stiffness of a ski, is type of fibre, content of fibre, matrix material, direction of reinforcement, core material and the adhesion between each material layer. Additionally, there are also the production conditions with all the varying parameters and the influence thereof on the final product.

Skis are produced by a pressing method where heat and pressure are introduced in the manufacture. The product and the material are created simultaneously, and natural variations are present that may be found in the finished final product. It always varies, but the size of and the extent of as well as the reason for the variations may be different between the skis. Skis may "be tailor-made" by theoretically dimensioning and constructing versus a certain stiffness and/or for obtaining a certain specific arching curve.

However, a difficulty is to measure and define an arching curve in the production. When the skis have been delivered to retailers, it is not possible to measure the arching, since measurement methods are lacking there. Lack of a clearly defined arching curve is a problem. Correct arching is spoken of, but it is not possible to display it graphically neither to define it at all. Neither there is any possibility of comparing the arching curve between an existing pair of skis for a specific snow condition, with the purpose of being able to sort out or distinguish a pair of new skis in a controllable way having specifically corresponding or specifically other properties.

The following actors represent the great interest:

Skiers, trainers, waxing-responsible persons, manufacturers, wholesale dealers, retailers.

Among skiers within the world elite, elite amateurs, amateurs, there is a great interest to be able to determine an arching curve specifically. This is for getting a possibility of optimising the relation between the sliding surface of the ski and the part of the ski that is coated with different waxes, with the purpose of providing grip upon the depression of the skier in an upward slope.

Among all skiers in the world, it is apprehended as the crucial thing to try out the correct arching for each skier. The curve of the arching affects, among other things, the length and the position where the grip wax should be coated on the running surface.

Elite skiers are occasionally forced to try up to a hundred of different skis before they can identify two skis that have similar properties and similar arching curve.

Today, two skis are placed beside each other on a planar ground, preferably indoors. The skier stands on the skis with the body weight evenly distributed between the two skis. The skier transfers the body weight to one of the skis with the purpose of trying to imitate the situation when you are skiing and intend to "tread" down the arching into contact for getting grip with the wax, after which the following is carried out:

A feeler gauge, usually 0.2 mm high, is brought by a hand from the rear part of the ski and forward until it "feels" like there is resistance and "sucks a little". After this operation, an approximate wax length is recommended empirically and arbitrarily, from the heel and forward to the approximate point of the ski where the feeler gauge contacts the ski, or it is recommended to try out another ski, etc. The skier then presses down the ski extra hard with the purpose of checking if the feeler gauge of 0.2 mm can be clamped, since this then should imitate when the same in the track treads down the ski into contact for providing grip by the fact that the grip wax meets the ground.

This is the method applied today in shops, at trainers and at other interested parties around the world.

In factories, it is, by means of traditional industrial measuring machines that are available in certain factories, possible to determine the measures of the arching by, e.g., a measuring probe. However, the different existing methods and machines are very expensive, involving investment levels of the order of hundreds of thousands of Swedish crowns up to millions. Furthermore, the method is very slow, which means that not all skis can be classified and marked because of the expense, no one or very few would buy them except for the world elite, which is forced to try ever so many skis, without knowing what kind of arching curve they have.

The experience and performance of the skier is substantially based on the arching, it is absolutely decisive and the basis for the skis to work at all and by grip wax applied under the arching be able to provide grip in an upward slope, simultaneously an optimally determined sliding surface.

NO SKIER KNOWS TODAY WHICH ARCHING CURVE IT HAS, SINCE THE CURVE/IMAGE OR THE CONCEPT DOES NOT EXIST AMONG THE SKIERS.

Not even at a producer of skis do two different persons know what is intended with arching curve or the mutual parameters thereof.

A diffuse so-called arching is something that is felt and experienced without dimensions or a clear description. Sometimes, the arching may be described as a linear measure, but it takes no consideration to the length at a specific load or the geometry of the curve as seen from the side at a specific load.

Examples of Consequences due to the Absence of an Efficient and Accurate Method to Determine and Define the Arching Curve Consequences, it is not possible today to measure an existing ski that feels relatively good and determine how the arching should be altered for offering optimum experience or performance at specific conditions in the ski track. Only by practical evaluation in ski tracks and opinions as well as crude judgements and after a hundred of tests, a desired result may possibly be achieved.

For the shop, this is time-consuming and it affects the economical result since more employees are required when skis are sold.

The skier gets no grip in the track, which results in the skis sliding backwards and a poorer skiing experience, as well as that one may be forced to discontinue due to becoming tired earlier and not managing the entire intended distance. The result for competing skiers becomes substantially poorer.

One may experience poor glide due to the fact that one treads down the arching into contact upon too low a load and then the skis "are jamming" and the grip wax disappears fast by wear after which they "slide backwards."

From the manufacturers to the retailers, there remain great stock volumes of skis that have not been sold because it has not been possible to try out and sell the same in a simple or fast way.

Everybody desires to be able to quickly and easily determine the very crucial arching curve with high accuracy, but no one can make this today easily, quickly or at low cost.

SUMMARY OF THE INVENTION

It is an object of the present invention to solve the above-mentioned problems.

According to the present invention, this is provided according to a first aspect by a measuring device for measuring the arching of an elongate body. The measuring device comprises an anvil member against which the elongate body is intended to be placed. Furthermore, the measuring device comprises a measure-collection member movable along the line of the longitudinal axis of the elongate body via a driving unit included in the measuring device, which measure-collection member is calibrated before measuring and is connected to a processor unit for the processing of measured values. Furthermore, the measuring device comprises a force-transmission member for applying a predetermined force (F), where $F \geqq 0$ N, to the elongate body, the applied force (F) being registered by means of a force-measuring member mounted on the force-transmission member. The measure-collection member measures, in abutment against and movement along the line of the longitudinal axis of the elongate body, continuously a length (y) and a height (x) between the elongate body and the measuring device, and delivers a digital signal to the processor unit, which calculates the arching. An advantage of this measuring device is that the arching can be measured fast, easily and with high accuracy. Another advantage of this measuring device is that it occupies little space and easily can be mounted vertically on, e.g., a wall or be placed horizontally for permanent use as well as temporary. The measuring device is calibrated very easily with high accuracy via a simple hand grip, without needing any previous knowledge about skiing or measuring of skis.

An additional advantage, in this connection, is obtained if the measuring device further comprises an input unit via which the predetermined force (F) is entered, as well as an actuator connected to the force-transmission member, the predetermined force (F) being applied by means of the actuator.

Furthermore, it is an advantage, in this connection, if the measuring device comprises a beam provided with a longitudinal groove in which the measure-collection member runs.

An additional advantage, in this connection, is obtained if the driving unit for the driving of the measure-collection member comprises a motor and notchedbelt drive.

According to another embodiment, an advantage is obtained if the driving unit for the driving of the measure-collection member comprises an electric motor having pulse and position transducers.

Furthermore, it is an advantage, in this connection, if the measuring device further comprises a stop member adjustable along the line of the longitudinal axis of the measuring device, against which stop member one short end of the elongate body is placed.

An additional advantage, in this connection, is obtained if the measuring device further comprises an interface member connected to the processor unit, to which interface, for instance, a display device and a printer may be connected.

The above-mentioned problems are also solved by means of a method for measuring the arching of an elongate body according to the present invention. The method is executed by means of a measuring device and comprises the steps of:

placing the elongate body against an anvil member included in the measuring device;

calibrating a measure-collection member included in the measuring device;

by means of a force-transmission member included in the measuring device applying a predetermined force (F) to the elongate body, where $F \geqq 0$ N;

by means of the measure-collection member, which abuts against and is moved along the elongate body, continuously measuring a length (y) and a height (x) between the elongate body and the measuring device; and that the measure-collection member delivers a digital signal to a processor unit included in the measuring device, which calculates the arching.

An advantage of this method is that it is possible to measure the arching fast, easily and with high accuracy. Another advantage is that the method is suitable both for permanent measuring as well as temporary measuring.

An advantage, in this connection, is obtained if the method further comprises the steps of:

by means of the force-transmission member applying a force ($F_{1/2}$) corresponding to a person's (y) half body weight, as well as by means of the measure-collection member measuring the arching ($A_{1/2}$) at this force ($F_{1/2}$);

by means of the force-transmission member applying a force ($F_1$) corresponding to the person's (y) entire body weight, as well as by means of the measure-collection member measuring the arching ($A_1$) at this force ($F_1$); and by means of the force-transmission member applying a force ($F_0$) that brings the arching ($A_0$) to zero, as well as registering this force ($F_0$).

Furthermore, it is an advantage, in this connection, if the method further comprises the step of:

moving the measure-collection member by a driving unit included in the measuring device.

An additional advantage, in this connection, is obtained if the method further comprises the step of:

entering said force (F) by means of an input unit included in the measuring device.

Furthermore, it is an advantage, in this connection, if the moving step comprises the step of:

moving the measure-collection member by a motor and notched-belt drive.

According to another embodiment, an advantage is obtained if the moving step comprises the step of:

moving the measure-collection member by an electric motor having pulse and position transducers.

An additional advantage, in this connection, is obtained if the method further comprises the step of:

placing the short end of the elongate body against a stop member adjustable along the line of the longitudinal axis of the measuring device.

Furthermore, it is an advantage, in this connection, if the method further comprises the step of:

connecting a display device and/or a printer to an interface member connected to the processor unit.

It should be pointed out that the denomination "comprises/comprising", when it is used in this application, is intended to specify the presence of stated features, steps or components, but does not exclude the presence of one or more other features, units, steps, components or groups thereof.

Embodiments of the invention will now be described with a reference to the accompanying drawings, where:

DETAILED DESCRIPTION OF EMBODIMENTS

Figure 1:
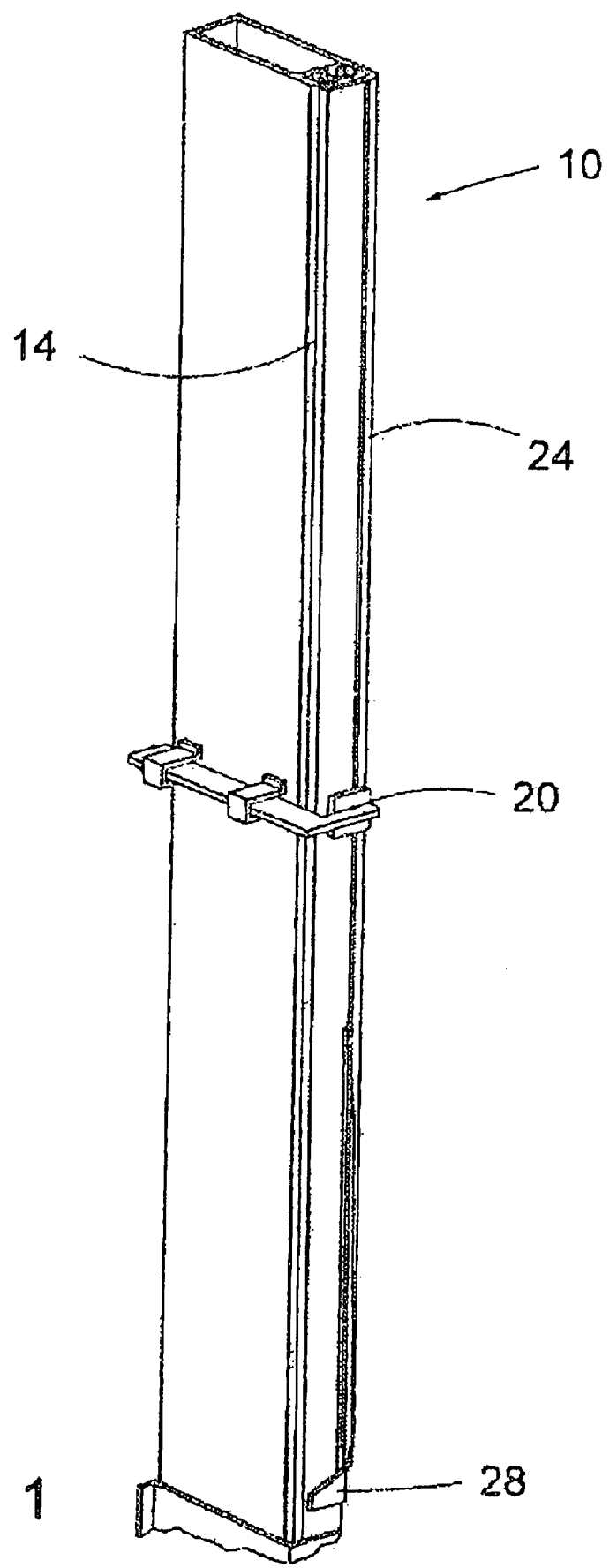
FIG. 1 shows a perspective view of a measuring device according to the present invention.
Figure 2:
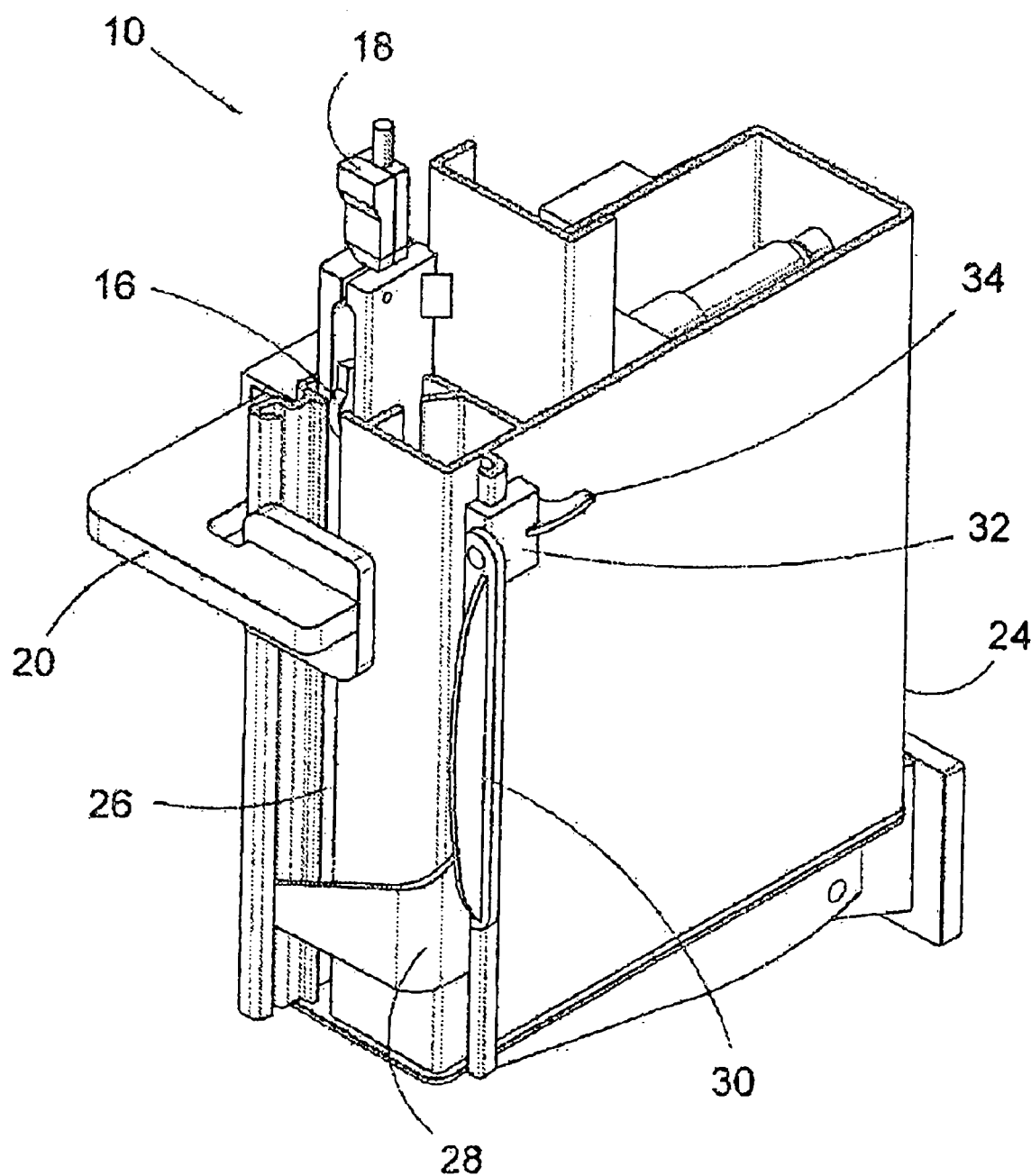
FIG. 2 shows a perspective view, partly in cross-section, of the measuring device shown in FIG. 1.
Figure 3:
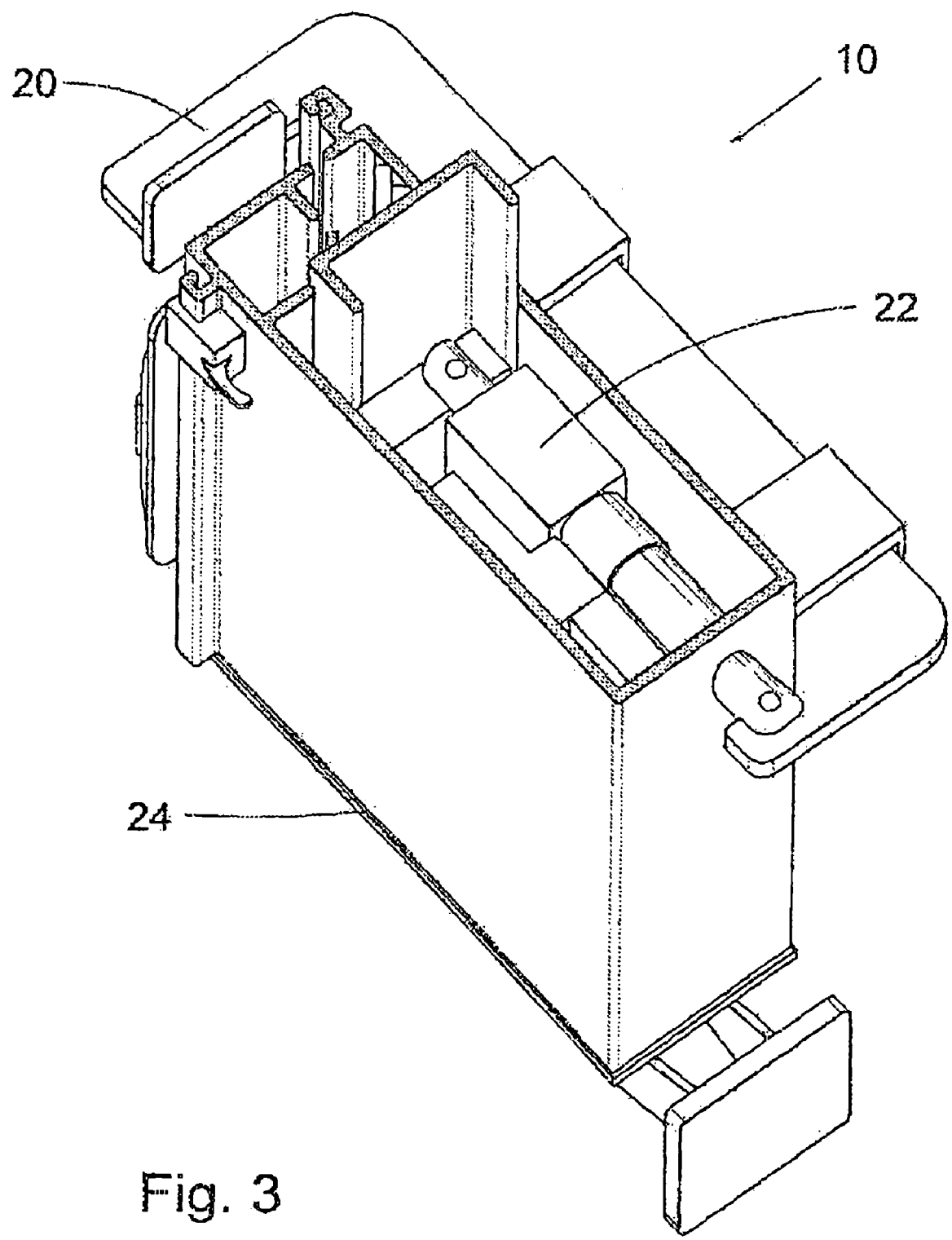
FIG. 3 shows another perspective view, partly in cross-section, of the measuring device shown in FIG. 1.
Figure 4:
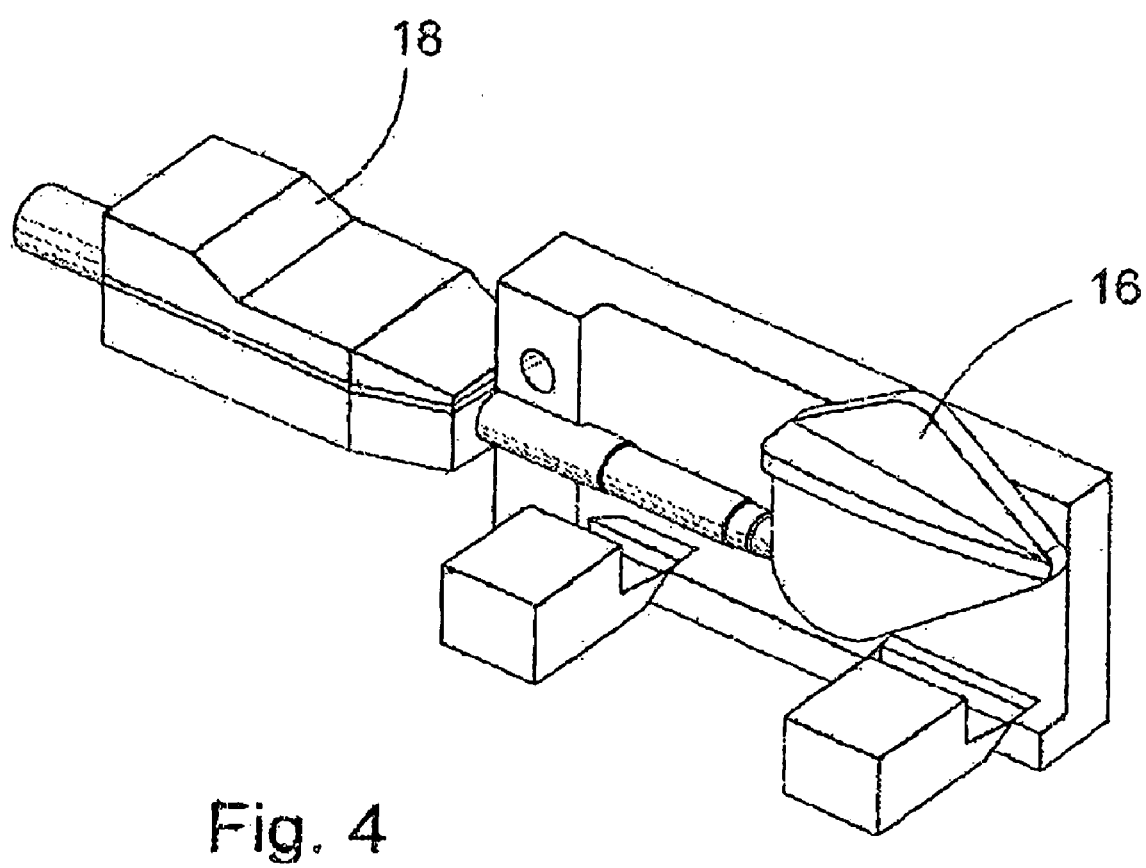
FIG. 4 shows a perspective view of, among other things, the measure-collection member included in the measuring device shown in FIG. 1.

In FIGS. 1-3, different perspective views are shown of a measuring device 10 for measuring the arching (A) of an elongate body 12. The elongate body 12 is not shown in FIGS. 1-4, but in FIG. 5. In FIGS. 2 and 3, the measuring device 10 is shown partly in cross-section. The measuring device 10 comprises an anvil member 14 against which the elongate body 12 is intended to be placed. Furthermore, the measuring device 10 comprises a measure-collection member 16, which is movable along the line of the longitudinal axis of the elongate body 12 via a driving unit (not shown) included in the measuring device 10. The measure-collection member 16 is connected to a processor unit 18 for the processing of measured values. The measure-collection member 16 is calibrated before measuring. Furthermore, the measuring device 10 comprises a force-transmission member 20 for applying a predetermined force (F), where $F \geq 0$ N, to the elongate body 12, the applied force (F) being registered by means of a force-measuring member mounted on the force-transmission member 20. The force-measuring member may, for instance, be strain gauges, a biased spring pile including electronic control for the registration of position and thereby force, or a cylinder provided with a piston, in which cylinder positive pressure is measured as a measure of the force. The measure-collection member 16 abuts against and moves along the line of the longitudinal axis of the elongate body 12 and measures continuously a length (y) and a height (x) (compare FIG. 5) between the elongate body 12 and the measuring device 10, and delivers a digital signal to the processor unit 18, which calculates the arching (A). Furthermore, the measuring device 10 comprises an input unit (not shown) via which the predetermined force (F) is entered. As is seen in FIG. 3, the measuring device 10 comprises an actuator 22 connected to the forcetransmission member 20. The predetermined force (F) is applied by means of the actuator 22.

Furthermore, the measuring device 10 comprises a beam 24 provided with a longitudinal groove 26 in which the measure-collection member 16 runs.

According to an embodiment, the driving unit for the driving of the measure-collection member 16 comprises a motor and notched-belt drive.

According to another embodiment, the driving unit for the driving of the measure-collection member 16 comprises an electric motor having pulse and position transducers.

Furthermore, the measuring device 10 comprises a stop member 28 adjustable along the line of the longitudinal axis of the measuring device 10, against which stop member one short end of the elongate body 12 is placed. Such as is seen, above all, in FIG. 2, the stop member 28 is connected to a bar 30 for the height adjustment of the stop member 28. The bar 30 is, in turn, connected to a brake carriage 32, which is connected to a brake lever 34, which is used for locking the stop member 28 at the suitable height.

Furthermore, the measuring device comprises an interface member (not shown) connected to the processor unit 18, to which interface, for instance, a display device and a printer may be connected.

Figure 5:
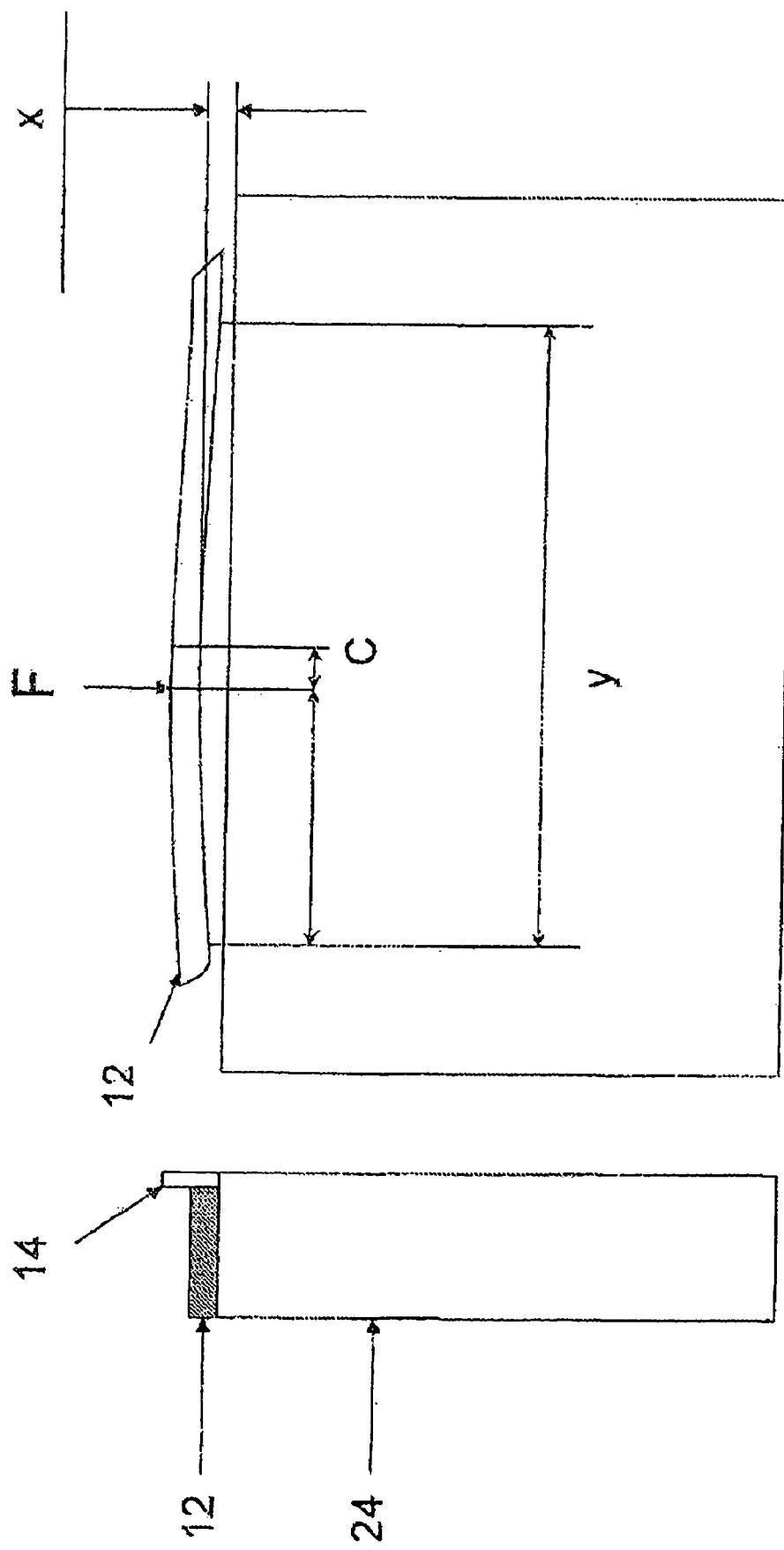
FIG. 5 schematically shows how the arching is measured of a ski.

In FIG. 5, it is schematically shown how the arching (A) is measured of an elongate body 12, here in the form of a ski 12. Such as has been indicated previously, x refers to the height between the ski 12 and the measuring device 10, and y refers to the length between the points of contact of the ski 12 with the measuring device 10. C refers to the points of balance of the ski 12, and F refers to the point where the force F is applied.

A reciprocating movement with a measuring probe that, from the inside of the beam, reads the height "x", the force F, points where "x" becomes zero, the distance A-B. The circular arc is calculated automatically by means of a computer unit mounted in the beam.

The measuring probe 16 transfers data from the running surface of the ski to a digital indicator 18, which reads the values continuously in the vertical direction, while a movement of the measuring probe 16 longitudinally with the ski is made automatically by means of only one control command from the computer unit. The longitudinal movement is provided by a motor and notched-belt drive or the like. An electric motor having pulse and position transducers drives the unit with the measuring probe that is mounted inside the beam. Via a groove 26 in the beam 24, the measuring probe 16 can collect data from the running surface of the ski.

The desired force is set via the input unit and is applied by means of an electric actuator 22. The requisite force when the arching is zero is measured, i.e., at the requisite pushing force when the skier treads through the arching.

The printer and display device can be connected. Data and results can be presented in the form of a curve as well as digits. Information about the position, length and geometry of the arching, i.e., the experience of the skier expressed as a graphical picture, waxing lengths, as well as positions are presented in selected ways. Data can be transferred wireless and via a fixed network to a database for comparisons, calculations and analysis. The measuring process lasts less than a minute.

By the fact that the device, locally or via a distributed computer network, can exchange data and information with a database, wireless or via a fixed connection, references from various measurements can be compared with the present measurement. This means that it does not matter where or by whom the measurement is carried out, the arching curves will always be comparable when the same concept definition is applied.

Experiences from a skier's earlier experiences of skis having other arching curves can be analysed and compared. Consideration to this may be given and the experience can be defined graphically from the arching curve of the desired ski.

Figure 6:
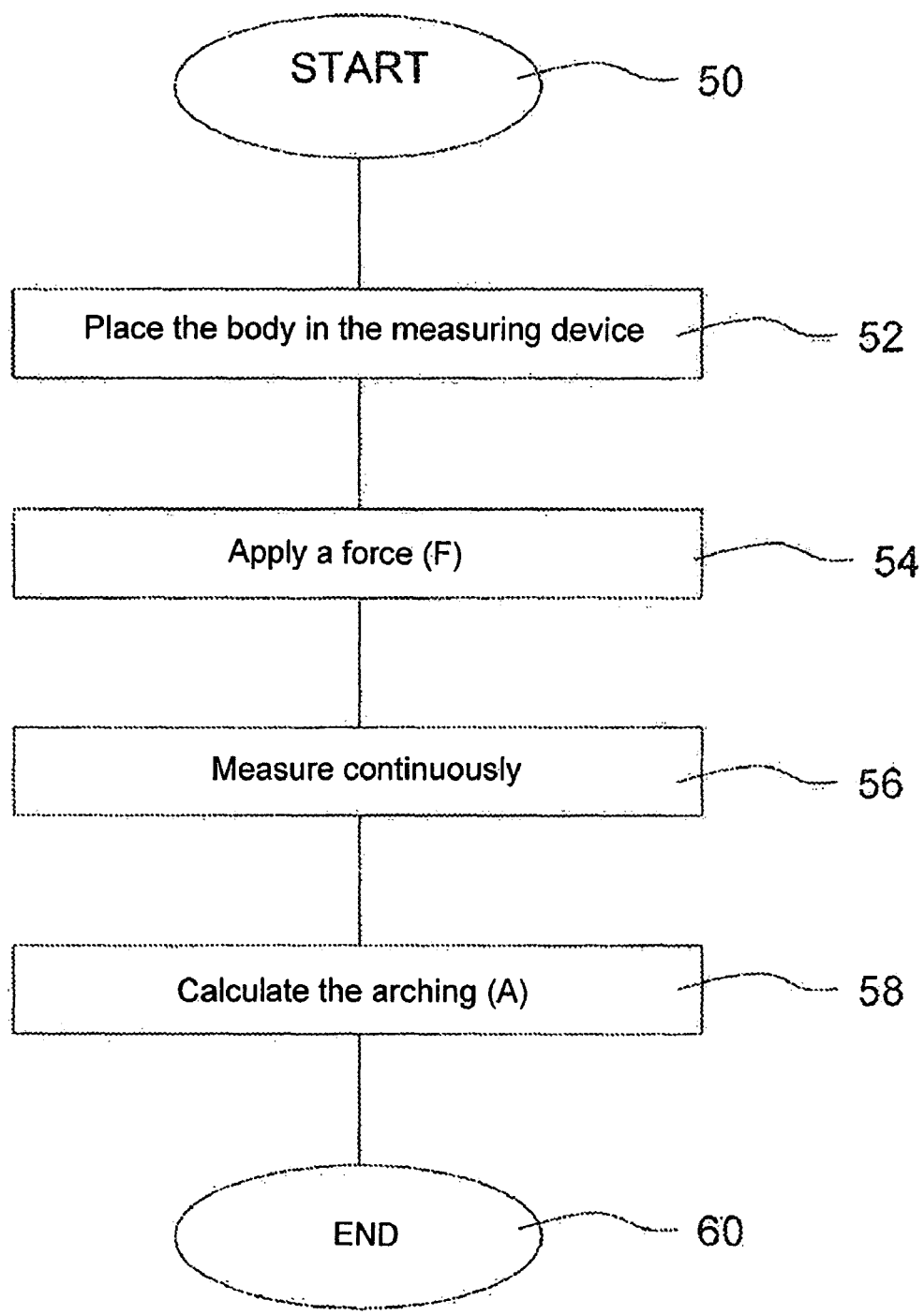
FIG. 6 is a flow chart of a method for measuring the arching of an elongate body according to the present invention.

In FIG. 6, a flow chart is shown of a method for measuring the arching (A) of an elongate body 12 according to the present invention. The method is executed by means of a measuring device 10 (compare FIGS. 1-5). The method begins at block 50. Next, the method continues, at block 52, with the step of: placing the elongate body 12 against an anvil member 14 included in the measuring device 10. The method then continues, at block 53, with the step of: calibrating a measure-collection member 16 included in the measuring device 10. The method then continues, at block 54, with the step of: by means of a force-trans-mission member 20 included in the measuring device 10 applying a predetermined force (F) to the elongate body 12, where $F \geq 0$ N. Next, the method continues, at block 56, with the step of: by means of the measure-collection member 16, which abuts against and is moved along the elongate body 12, continuously measuring a length (y) and a height (x) between the elongate body 12 and the measuring device 10. The method then continues, at block 58, with the step of: that the measure-collection member 16 delivers a digital signal to a processor unit 18 included in the measuring device 10, which processor unit 18 calculates the arching (A). The method is terminated at block 60.

Figure 7:
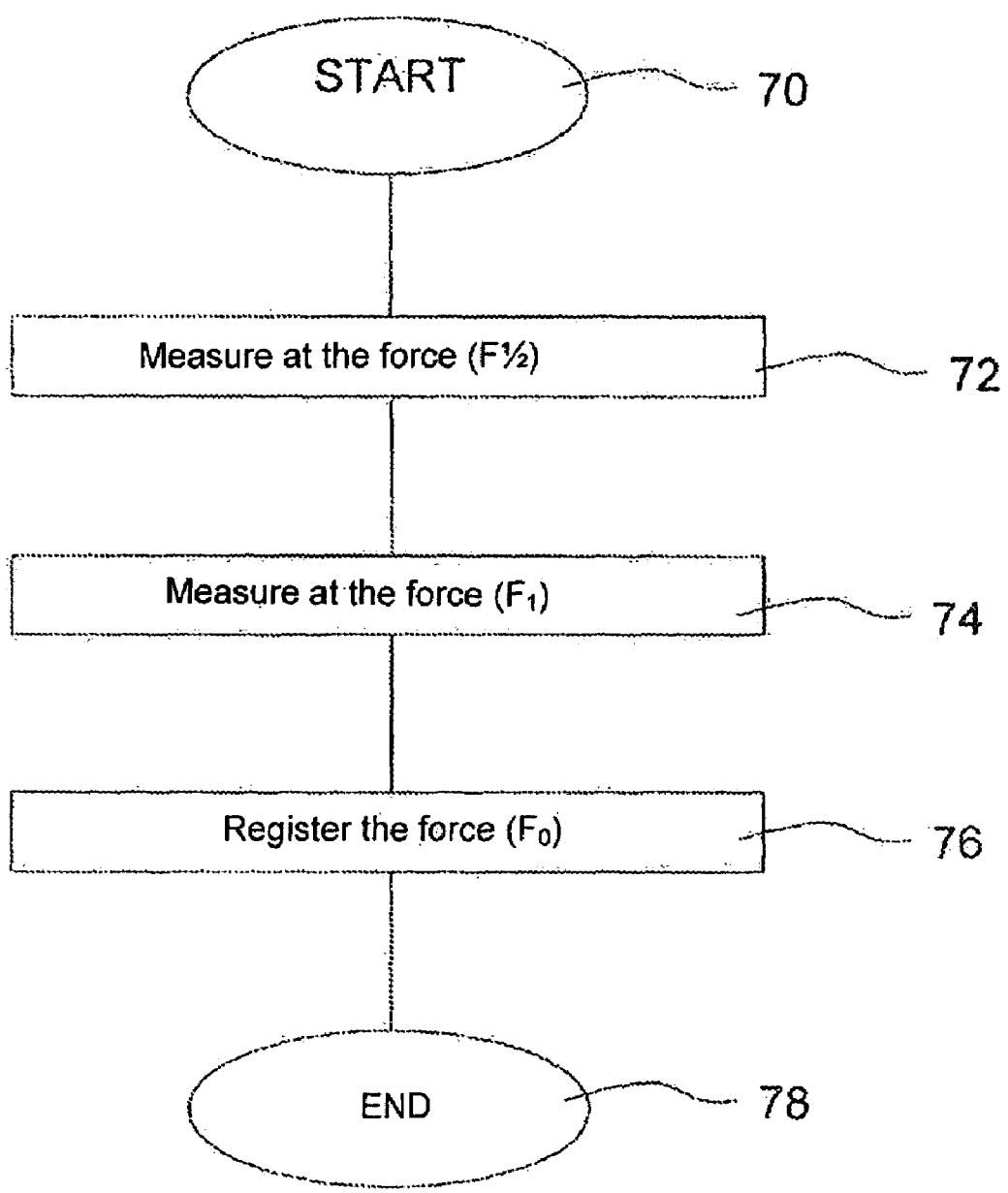
FIG. 7 is a flow chart of further steps that may be comprised in the method when the elongate body is a ski.

In FIG. 7, a flow chart is shown of further steps that may be comprised in the method when the elongate body 12 is a ski 12. The method begins at block 70. Next, the method continues, at block 72, with the step of: by means of the force-transmission member 20 applying a force ($F_{1/2}$) corresponding to a person's (P) half body weight, as well as by means of the measure-collection member 16 measuring the arching ($A_{1/2}$) at this force ($F_{1/2}$). The method then continues, at block 74, with the step of: by means of the force-transmission member 20 applying a force ($F_1$) corresponding to the person's (P) entire body weight, as well as by means of the measure-collection member 16 measuring the arching ($A_1$) at this force ($F_1$). Next, the method continues, at block 76, with the step of: by means of the force-transmission member 20 applying a force ($F_0$) that brings the arching ($A_0$) to zero, as well as registering this force ($F_0$). The method is terminated at block 78.

According to a preferred embodiment of the method, it furthermore comprises the step of: registering the applied force by means of a force-measuring member mounted on the force-transmission member 20. The force-measuring member may, for instance, be strain gauges, a biased spring pile including electronic control for the registration of length and thereby force, or a cylinder provided with a piston, in which cylinder positive pressure is measured as a measure of the force.

According to a preferred embodiment of the method, it furthermore comprises the step of: moving the measure-collection member 16 by a driving unit included in the measuring device 10.

According to a preferred embodiment of the method, it furthermore comprises the step of: entering the force (F) by means of an input unit included in the measuring device 10.

According to a preferred embodiment of the method, it furthermore comprises the step of: moving the measure-collection member 16 by a motor and notched-belt drive.

According to another embodiment of the method, it furthermore comprises the step of: moving the measure-collection member 16 by an electric motor having pulse and position transducers.

According to a preferred embodiment of the method, it furthermore comprises the step of: connecting a display device and/or a printer to an interface member connected to the processor unit 18.

It should be pointed out that the measurement by means of the measuring device 10 may be carried out by a robot or a human being.

The invention is not limited to the embodiments described above. It is evident that many different modifications are feasible within the scope of the following claims.

The invention claimed is:

1. A measuring device for measuring the arching (A) of an elongate body, characterized in that the measuring device comprises an elongate beam provided with an elongate anvil member against which one long side of the elongate body is intended to be placed, a measure-collection member movable along the line of the longitudinal axis of the elongate body via a driving unit included in the measuring device, which measure-collection member is calibrated before measuring and is connected to a processor unit for the processing of measured values, the measuring device furthermore comprising a force-transmission member for applying a predetermined force (F) directed toward the beam, where $F \geq N$, to the elongate body near the point of balance (C) of the elongate body, the applied force (F) being registered by means of a force-measuring member mounted on the force-transmission member, the measure-collection member, in abutment against and movement along the line of the longitudinal axis of the elongate body, continuously measuring a length (y) and a height (x) between the elongate body and the measuring device, where y refers to the length between the points of contact of the elongate body with the measuring device, and delivering a digital signal to the processor unit, which calculates the arching (A).

2. Measuring device according to claim 1, characterized in that the measuring device furthermore comprises an input unit via which the predetermined force (F) is entered, as well as an actuator connected to the force-transmission member, the predetermined force (F) being applied by means of the actuator.

3. Measuring device according to claim 1, characterized in that the beam is provided with a longitudinal groove in which the measure-collection member runs.

4. Measuring device according to claim 1 characterized in that the driving unit for the driving of the measure-collection member comprises a motor and notched-belt drive.

5. Measuring device according to claim 1 characterized in that the driving unit for the driving of the measure-collection member comprises an electric motor having pulse and position transducers.

6. Measuring device according to claim 1 characterized in that the measuring device furthermore comprises a stop member adjustable along the line of the longitudinal axis of the measuring device, against which stop member one short end of the elongate body is placed.

7. Measuring device according to claim 1 characterized in that the measuring device furthermore comprises an interface member connected to the processor unit.

8. A method for measuring the arching (A) of an elongate body by means of a measuring device, which method comprises the steps of:

placing one long side of the elongate body against an elongate anvil member included in the measuring device and arranged along an elongate beam included in the measuring device;

calibrating a measure-collection member included in the measuring device;

by means of a force-transmission member included in the measuring device applying a predetermined force (F), directed toward the beam, to the elongate body near the point of balance (C) of the elongate body, where $F \geq 0$ N;

by means of the measure-collection member, which abuts against and is moved along the elongate body, continuously measuring a length (y) and a height (x) between the elongate body and the measuring device, where y refers to the length between the points of contact of the elongate body with the measuring device; and that the measure-collection member delivers a digital signal to a processor unit included in the measuring device, which process unit calculates the arching (A).

9. Method for measuring the arching (A) of an elongate body according to claim 8, characterized in that the method furthermore comprises the steps of:

by means of the force-transmission member applying a force ($F_{1/2}$) corresponding to a person's (P) half body weight, as well as by means of the measure-collection member measuring the arching ($A_{1/2}$) at this force ($F_{1/2}$);

by means of the force-transmission member applying a force ($F_1$) corresponding to the person's (P) entire body weight, as well as by means of the measure-collection member measuring the arching ($A_1$) at this force ($F_1$); and by means of the force-transmission member applying a force ($F_0$) that brings the arching ($A_0$) to zero, as well as registering this force ($F_1$).

10. Method for measuring the arching (A) of an elongate body according to claim 8, characterized in that the method furthermore comprises the step of:

moving the measure-collection member by a driving unit included in the measuring device.

11. Method for measuring the arching (A) of an elongate body according to claim 8 characterized in that the method furthermore comprises the step of:

entering said force (F) by means of an input unit included in the measuring device.

12. Method for measuring the arching (A) of an elongate body according to claim 10, characterized in that the moving step comprises the step of: moving the measure-collection member by a motor and notched-belt drive.

13. Method for measuring the arching (A) of an elongate body according to claim 10, characterized in that the moving step comprises the step of:

moving the measure-collection member by an electric motor having pulse and position transducers.

14. Method for measuring the arching (A) of an elongate body according to claim 8 characterized in that the method furthermore comprises the step of:

placing the short end of the elongate body against a stop member adjustable along the line of the longitudinal axis of the measuring device.

15. Method for measuring the arching (A) of an elongate body according to claim 8 characterized in that the method furthermore comprises the step of:

connecting a display device and/or a printer to an interface member connected to the processor unit.

* * * * *